United States Patent [19]

Ishida et al.

[11] Patent Number: 5,827,718
[45] Date of Patent: Oct. 27, 1998

[54] LIPASE, MICROORGANISMS PRODUCING THE LIPASE, METHOD OF PRODUCING THE LIPASE AND USE OF THE LIPASE

[75] Inventors: Reiko Ishida, Yokohama; Masahiro Suzuki, Chiba; Takashi Kotsuka, Chiba; Kazunori Sakimoto, Chiba, all of Japan

[73] Assignee: Novo Nordisk A/S, Bagsvaerd, Denmark

[21] Appl. No.: 605,015

[22] PCT Filed: Aug. 26, 1994

[86] PCT No.: PCT/JP94/01416

§ 371 Date: Mar. 14, 1996

§ 102(e) Date: Mar. 14, 1996

[87] PCT Pub. No.: WO95/06720

PCT Pub. Date: Mar. 9, 1995

[30] Foreign Application Priority Data

Aug. 30, 1993 [JP] Japan .................................. 5-214506

[51] Int. Cl.$^6$ ....................................................... C12N 9/20
[52] U.S. Cl. ........................... 435/198; 435/183; 435/188; 435/196; 435/264; 435/874; 252/174.12; 530/350; 530/825; 424/260.1; 424/94.1
[58] Field of Search ..................................... 530/350, 825; 252/174.12; 424/260.1, 94.1; 435/183, 188, 196, 198, 264, 874

[56] References Cited

U.S. PATENT DOCUMENTS 4,933,287  6/1990  Farin .
5,059,341  10/1991  Holmes .
5,063,160  11/1991  Holmes .

FOREIGN PATENT DOCUMENTS 0571982  12/1993  European Pat. Off. .
62-210987  9/1987  Japan .

OTHER PUBLICATIONS

Hans Andree, Wolf–R Müller and Rolf D. Schmid, Lipases as Detergent Components. J. Appl. Biochem. 2, 218–229 (1980).

*Primary Examiner*—Paula K. Hutzell
*Assistant Examiner*—Khalid Masood
*Attorney, Agent, or Firm*—Steve T. Zelson, Esq.; Valeta Gregg, Esq.

[57] ABSTRACT

Bacteria belonging to the genus Pseudomonas, alkaline lipase produced by the bacteria and having the following properties, a method of producing the lipase, and detergent compositions containing the lipase:

(1) Operating pH and optimum pH
   an operating pH is in the range of from 3.5 to 12 and an optimum pH is in the range of from 10 to 11 using a triolein emulsion as a substrate;

(2) Operating temperature and optimum temperature
   an operating temperature is in the range of from 30° C. to 80° C. and an optimum temperature is in the range of from 55° C. to 65° C. using the triolein emulsion as a substrate;

(3) Molecular weight
   a molecular weight measured by SDS-polyacrylamide gel electrophoresis is 31,000±2,000; and (4) Isoelectric point
   an Isoelectric point measured by isoelectric point polyacrylamide gel electrophoresis is 5.2±0.5.

The lipase has high stability against detergent components such as surfactants, protease, etc. and can be blended together with protease with detergents. Further, the lipase suffers less inhibition of its activity, so that it can enhance the washing power of detergents containing it.

7 Claims, 4 Drawing Sheets

LIPASE, MICROORGANISMS PRODUCING THE LIPASE, METHOD OF PRODUCING THE LIPASE AND USE OF THE LIPASE

This application is a 371 of PCT/JP94/0146 filed Aug, 26, 1994.

TECHNICAL FIELD

This invention relates to a novel lipase, to microorganisms producing the lipase, to a method of producing the lipase, and to use of the lipase. More particularly, this invention relates to the lipase which bacteria belonging to the genus Pseudomonas produce and which has activity in washing liquids (in alkaline regions), to microorganisms producing the lipase, to a method of producing the lipase, and to detergent compositions containing an enzyme or enzymes which can decompose lipids in the washing liquids.

BACKGROUND ART

It has been known to utilize enzymes for blending them with detergents in order to improve the washing efficiency in washing. For example, it has been known to blend proteases with detergent compositions to decompose and remove proteins and other dirt on articles to be washed, to blend cellulases with detergent compositions to remove dirt on cellulose fabrics to be washed, or to blend polysaccharide decomposing enzymes such as amylase to decompose and remove polysaccharides and other dirt attached on articles to be washed. In addition, recently, it has been known that blending lipases with detergents can decompose and remove lipids on articles to be washed so that the washing efficiency can be increased. This use is described by H. Andree et al., in the report "Lipase as detergent components," Journal of Applied Biochemistry, 2, 218–229 (1980) and so on.

Preferred lipases for detergents are those which exhibit their lipase activities sufficiently in washing liquids. Under ordinary washing conditions, the pH of the washing liquid is in alkaline range and, hence, lipases are required which function in alkaline pH range. Generally, lipid dirt is known to be relatively easy to remove under the conditions of high temperature and high alkalinity while it is impossible to sufficiently remove by washing at low temperatures (not higher than 60° C.). Not only in Japan where washing is being done mainly at lower temperatures but also in European countries and the United States, washing temperatures tend to be decreased. Therefore, preferred lipases for detergents must function sufficiently even at low temperatures. In addition, preferred lipases for detergents should exhibit their function upon washing even in the presence of detergent components such as surfactants as well as proteases and bleaching agents as contained in many detergents. Furthermore, preferred lipases for detergents, when they are stored in a state blended in detergents, should be stable against components copresent in the detergents. Accordingly, there is a desire for development of detergent compositions which contain lipases with the above-described preferred features and have high washing effect against lipid dirt.

Lipases produced by microorganisms include those derived from microorganisms belonging to the genera Pseudomonas, Alcaligenes, Achromobacter, Mucor, Candida, Humicola, etc.

However, most lipases obtained from these strains have their optimum pH in the regions of from neutral to weak alkaline so that they do not function sufficiently in detergent solutions in alkaline regions and show low stability in the detergent solutions.

Further, the respective lipases derived from the microorganisms belonging to the genera Achromobacter, Candida, Mucor, and Humicola suffer strong inhibition of their activities in the presence of anionic surfactants.

It has been widely known that microorganisms belonging to the genus Pseudomonas produce lipases. The strains of the genus Pseudomonas include *Ps. fluorescens, Ps. cepacia, Ps. fragi, Ps. alcaligenes*, and *Ps. pseudoalcaligenes, Ps. aeruginosa*. The known lipases obtained from these strains do not satisfy the above-described characteristics.

OBJECT OF THE INVENTION

Accordingly, an object of this invention is to provide a lipase which functions sufficiently in washing liquids, whose activity is not inhibited substantially by components copresent in the detergent, and which shows high stability against other components of the detergent, such as a surfactant, a protease and the like, a microorganism producing such a lipase, and a method of producing such a lipase.

Another object of this invention is to provide a detergent composition which contains the above-described lipase as a washing aid and an enzyme-containing detergent composition containing in addition to the above-described lipase one or more other enzymes such as protease.

SUMMARY OF THE INVENTION

In order to obtain the lipase having the above-described characteristics, the present inventors isolated a number of microorganisms and cultivated for screening. As a result, the inventors found that strains belonging to the genus Pseudomonas, as represented by Pseudomonas sp. SD705 isolated from the soil in a suburb of Tokyo, produce a novel lipase useful for detergents, thus completing this invention.

This invention, relates to a novel lipase which is produced by a microorganism or variants belonging to the genus Pseudomonas, which acts over the whole active pH range measured of from pH 3.5 to 12, and which has an optimum temperature of about 55° to 65° C.

Also, this invention relates to a method of producing the lipase, to novel microorganisms producing the lipase, and to detergent compositions containing the lipase.

DETAILED DESCRIPTION OF THE INVENTION

Producing Microorganisms

Figure 1:
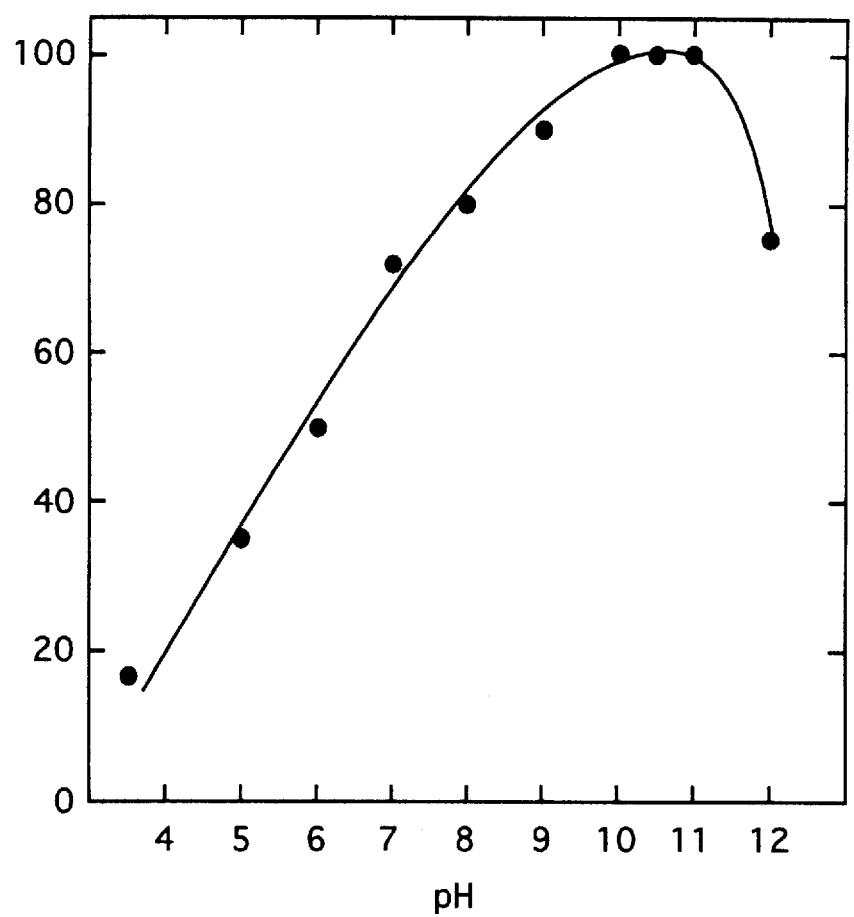
FIG. 1 is a graph illustrating the relation between the reaction pH and relative activity of the lipase produced by the strain SD705 of this invention.

Microorganisms which can be used for producing the lipase of this invention are not limited particularly as far as they can produce the lipase having the properties described hereinbelow and they are bacteria belonging to the genus Pseudomonas having the taxonomic properties described hereinbelow. Such bacteria can be selected from the stored strains or those microorganisms which are newly isolated from the nature. Spontaneous and artificial variants of these bacteria may of course be included by the microorganisms of this invention as far as they have productivity of lipases having the properties described below. Such bacterial strains can be isolated from soils or other sources for isolation by conventional methods. The objective strains can be screened by cultivating microorganisms to be tested in, for example, a conventional cultivation medium for bacteria and determining the activity of lipase in the culture broth under the conditions of high pH and normal temperature by a conventional method.

An example of the strains which belong to the genus Pseudomonas and produce the novel lipase of this invention is the SD705 strain which the present inventors isolated from the soil of a suburb of Tokyo.

The SD705 strain has the bacteriological properties shown in Table 1 below. In Table 1 are also described the bacteriological properties of *Pseudomonas alcaligenes* and of *Pseudomonas pseudoalcaligenes* which are relatively similar to those of the bacteria of this invention referring to Bergey's Manual of Systematic Bacteriology, 1984.

Further, quantitative DNA hybridization was performed on ATCC 909, type strain of *Pseudomonas alcaligenes*, and ATCC 17440, type strain of *Pseudomonas pseudoalcaligenes*, according to the teaching of Nippon Saikingaku Zasshi, 45(5), 1990. The results show that the strain SD705 shows less than 30% homology to the type strains. From these results, the strain of this invention was identified to be a novel species close to *Pseudomonas alcaligenes* belonging to the genus Pseudomonas.

The strain of this invention was deposited at National Institute of Bioscience and Human-Technology, Agency of Industrial Science and Technology and was assigned accession number FERM P-13781, and transferred to deposition under the international deposition system according to Budapest Treaty on the International Recognition of the Deposit of Microorganisms for the Purposes of Patent Procedure and was assigned accession number FERM BP-4772.

Variants obtained from the above-described strains as a mother strain by spontaneous or induced mutation can also be used as the lipase producing microorganisms according to this invention.

Methods for preparing the above-described variants include, for example, conventional methods such as a method comprising spreading the mother strain cells on an

TABLE 1

|  | SD705 Strain | *Pseudomonas alcaligenes* | *Pseudomonas pseudoalcaligenes* |
| --- | --- | --- | --- |
| (1) Morphology | Rods | Rods | Rods |
| (2) Gram stain | Negative | Negative | Negative |
| (3) Spore | None | None | None |
| (4) Mobility | Yes | Yes | Yes |
| (5) Flagella | Polar monotrichous | Polar monotrichous | Polar monotrichous |
| (6) Oxidase | Positive | Positive | Positive |
| (7) Catalase | Positive | Positive | Positive |
| (8) Production of fluorescent pigment | No | No | No |
| (9) Accumulation of PHB | Negative | Negative | d |
| (10) Arginine dihydrolase | Negative | Positive | d |
| (11) Growth at 41° C. | Possible | Possible | Possible |
| (12) Denitrification | Negative | Positive | d |
| (13) Gelatin Liquefaction | Negative | d | d |
| (14) Decomposition of starch | Negative | Negative | Negative |
| (15) Assimilability of glucose | Negative | Negative | Negative |
| (16) Assimilability of L-aspartate | Negative | Negative | Negative |
| (17) Assimilability of L-glutamate | Positive | Positive | Positive |
| (18) Assimilability of D-gluconate | Negative | Negative | d |
| (19) Assimilability of L-histidine | Negative | d | d |
| (20) Assimilability of ethanolamine | Negative | Negative | Positive |
| (21) Assimilability of n-butanol | Positive | d | Positive |
| (22) Assimilability of isobutanol | Negative | d | Negative |
| (23) Assimilability of glycerol | Negative | Negative | d |
| (24) Assimilability of sorbitol | Negative | Negative | d |
| (25) Assimilability of itaconic acid | Negative | Negative | d |
| (26) Assimilability of mesaconic acid | Negative | Negative | Positive |
| (27) Assimilability of β-hydroxybutyrate | Positive | Negative | Positive |
| (28) Assimilability of betaine | Negative | Negative | Positive |
| (29) Assimilability of fructose | Negative | Negative | Positive |
| (30) Assimilability of glycerate | Negative | Negative | Positive |
| (31) GC content (%) | 60 | 64–68 | 62–64 | d: 11–89% of the strains belonging to the species concerned is positive.

As shown in Table 1, the SD705 strain differs from *Pseudomonas pseudoalcaligenes* in the assimilability of ethanolamine, mesaconic acid, betaine, fructose, and glycerate and from Pseudomonas alcaligenes in the presence or absence of arginine dihydrolase, presence or absence of denitrification, the assimilability of β-hydroxybutyrate while the SD705 strain has lower GC content than both *Pseudomonas alcaligenes* and *Pseudomonas pseudoalcaligenes* strains.

agar medium containing an oil such as olive oil without artificial mutation treatment by irradiation with ultraviolet ray or with a chemical such as N-methyl-N'-nitro-N-nitrosoguanidine (NTG) or the like, or after such a treatment, screening from the growing strains those which form larger clear zones around the colonies, and cultivating the screened strains in a lipase production medium, thereby screening the most productive strain.

The lipase producing microorganisms of this invention preferably are those strains which show 50% or more, more preferably 70% or more, homology to the SD705 strain in DNA hybridization.

Method for Preparation

The lipase of this invention is excreted mainly out of the bacterial cells (into the culture medium) by cultivating the lipase producing microorganisms of this invention.

As nutrient sources for the culture medium, a wide variety of those conventionally used in cultivation can be used. Carbon sources may be assimilable hydrocarbons or materials containing them. For example, there can be used oils and fats, corn steep liquor, Tween surfactants, and so on. Nitrogen sources may be assimilable nitrogen compounds or materials that contain them. For example, there can be used ammonium salts, nitrates, soybean powder, meat extract, corn steep liquor, pharmamedia, and so on. Inorganic salts such as phosphates, e.g., diammonium hydrogenphosphate and dipotassium hydrogenphosphate, magnesium salts, calcium salts, manganese salts, and the like may be added optionally.

Cultivation conditions may vary more or less depending on the composition of the culture media, which conditions may be those suited for the production of the lipase of this invention. Usually, the following conditions are selected. That is, the culture temperature is in the range of from 10° to 40° C., preferably from 20° to 37° C. The culture time is from about 8 hours to 100 hours, and the cultivation may be completed when the production of the lipase of this invention reached to the maximum level. The pH of the culture medium may be 5 to 12, with pH of 7 to 10 being preferred for the production of the lipase of this invention. By such a cultivation, the objective lipase is produced out of the bacterial cells (into the culture medium).

Separation and Purification Method

Collection of the lipase of this invention obtained in the above-described manner can be separated and purified by conventional methods for collecting lipases.

More specifically, the lipase of this invention can be obtained by using a single or a combination of a plurality of separation or purification means such as a conventional filtration or centrifugation method in which bacterial cells or solid components of the culture medium are separated from the culture broth to isolate a supernatant or filtrate, with or without concentrating such a separated liquid, a salting out method in which soluble salts are added to the separated liquid to precipitate enzymes, an organic solvent precipitation method in which a hydrophilic organic solvent is added to precipitate enzymes or contaminants, an absorption and desorption method using an ion exchange resin, a gel filtration method, a spraying and drying method with or without adding an stabilization aid, a freezing and drying method, and so on.

Method for Measuring Activity of Enzymes

In this invention, measurement of lipase activity was performed using a method in which triolein-polyvinyl alcohol (PVA) emulsion was used as a substrate.

More specifically, the measurement of activity was carried out in the following manner.

A mixture of 0.1 ml of an enzyme solution, 0.4 ml of a buffer solution consisting of 1 mM calcium chloride, 100 mM ε-aminocaproic acid, 100 mM bistris(bis[2 [hydroxyethyl]-iminotris[hydroxymethyl]methane) and 100 mM TAPS (N-tris[hydroxymethyl]methyl-3-aminopropanesulfonic acid), the buffer solution being adjusted to pH 10.0 with sodium hydroxide, and 0.5 ml of triolein emulsion was incubated at 37° C. for 10 minutes for reaction in a test tube with a stopper, and the reaction was stopped with 0.2 ml of 1N hydrochloric acid as a reaction stopping agent. The triolein emulsion used was a homogenate of a mixture of 10 ml of an aqueous 2% polyvinyl alcohol (PVA) solution (Poval PVA117 (trade name of Kuraray Co.) : Poval PVA205 (trade name, Kuraray Co.)= 9:1 (W/W)) and 2.5 g of triolein. After the reaction was stopped, 2 ml of n-hexane, 2 ml of isopropyl alcohol, and 1 ml of distilled water were added to the reaction mixture and the mixture was stirred vigorously. After standing, the hexane layer was sampled and the amount of oleic acid was determined by the TLC-FID method (Minagawa et al., Lipids, 18, 732 (1983)). The unit of activity was defined such that the amount of the enzyme which produces 1 micro mole of oleic acid for 1 minute was 1 unit (1U).

The activity of the protease blended with the detergent in the examples described hereinbelow was measured by the measurement method described in Japanese Patent Publication (Kokoku) No. 60-55118 (1985) and the unit of activity was expressed in nanokatal (nkatal=10-9 katal, abbreviated as "nkat").

Properties of Enzymes

The lipase of this invention has the following properties. That is, the properties of the lipase produced by Pseudomonas sp. SD705, the strain of this invention, will be described below.

(1) Action

It acts on triglycerides and hydrolyze the esters.

(2) Substrate specificity

It hydrolyzes a wide variety of glycerides and esters.

As the glyceride substrate, emulsion of each glyceride-gum Arabic was used. The emulsion used was a homogenized emulsion of 10 g of a glyceride, 10 g of gum Arabic, and 100 g of distilled water.

A mixture of 5 ml of the above-described emulsion, 5 ml of 10 mM Tris buffer solution (pH 10.0) containing 100 mM sodium chloride and 25 mm calcium chloride, 4.5 ml of distilled water, and 0.5 ml of an enzyme solution was reacted at 30° C. and at pH 10, and the rate of fatty acid formation was determined by a pH stat titration method with 0.05N sodium hydroxide. The rate of fatty acid formation was taken as a decomposition activity of each substrate.

Assuming the decomposition activity of the lipase for triolein is 100, the lipase showed relative activity of 125 for tributyrin, 55 for olive oil, 70 for Soybean oil, and 66 for cotton seed oil.

The decomposition activities of the lipase for esters were determined by colorimetry (OD405) of p-nitrophenol produced by hydrolysis reaction at pH 8.0 and at 30° C. of p-nitrophenyl fatty acid ester as a substrate.

Assuming the decomposition activity of pNPP (p-nitrophenyl palmitate) is 100, the lipase showed relative activity of 134 for pNPL (p-nitrophenyl laurate), and 34 for p-NPV (p-nitrophenyl valerate).

(3) Operating pH and optimum pH

Operating pH and optimum pH were determined by the above-described method for the measurement of activity with triolein emulsion as a substrate. These were measured at different pH values upon reaction ranging from 3.5 to 12.0. As the buffer solution was used a mixed buffer solution consisting of 1.0 mM calcium chloride, 100 mM ε-aminocaproic acid, 100 mM bistris(bis[2-hydroxyethyl] iminotris[hydroxy-methyl]methane), and 100 mM TAPS (N-tris[hydroxymethyl]-methyl-3-aminopropanesulfonic acid), with the pH of the buffer solution being adjusted with hydrochloric acid or sodium hydroxide. The relation between the reaction pH and relative activity was as shown in FIG. 1. When measured in the range of pH 3.5 to 12, the operating pH was in the range of 3.5 to 12 while the optimum pH was in the range of 10 to 11.

(4) Operating temperature and optimum temperature

Figure 2:
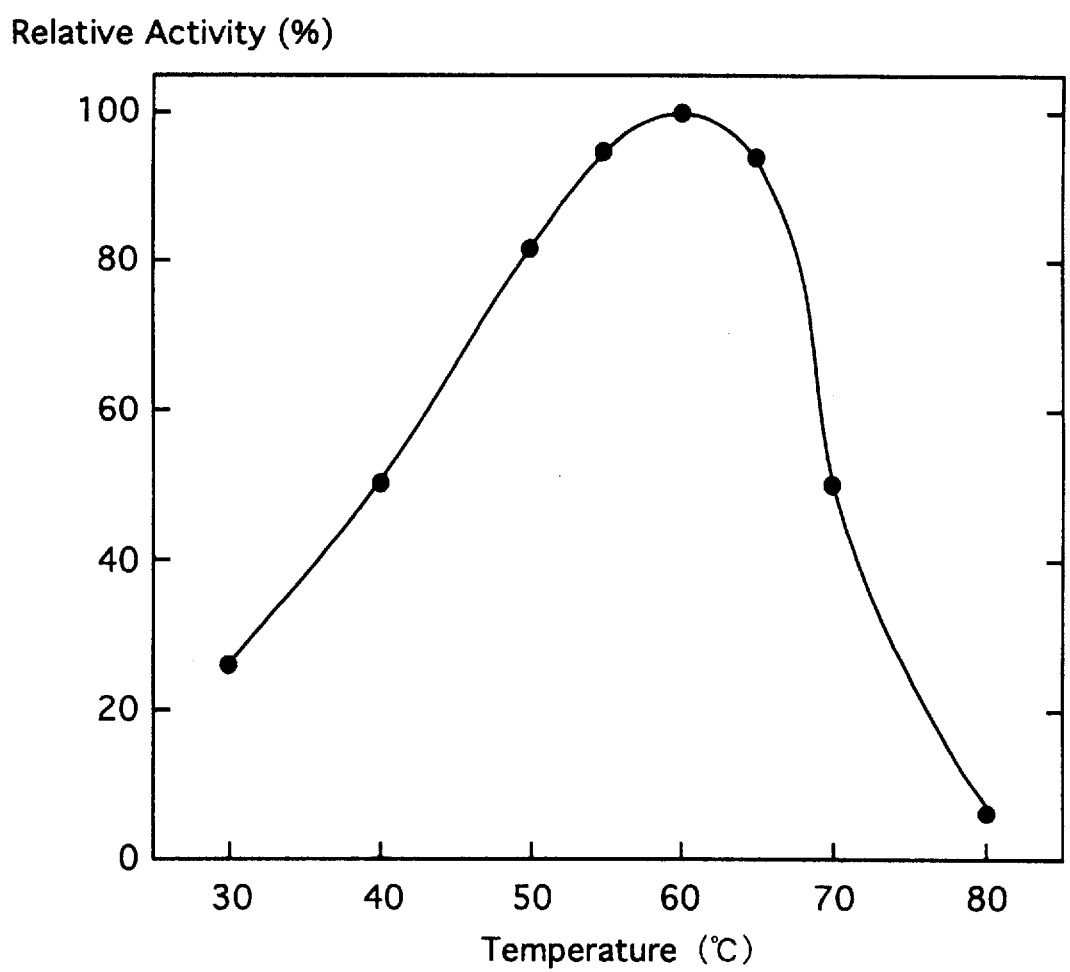
FIG. 2 is a graph illustrating the relation between the reaction temperature and relative activity of the lipase produced by the strain SD705 of this invention.

Operating temperature and optimum temperature were measured in the same manner as the method for measurement of activity described above except that the reactions were performed at different reaction temperatures in the range of from 30° C. to 80° C. with triolein emulsion as a substrate. The relation between the reaction temperature and relative activity was as shown in FIG. 2. When measured at 30° C. to 80° C., the operating temperature was in the range of from 30° C. to 80° C. while the optimum temperature was in the range of from 55° C. to 65° C. At 40° C. and 70° C., the relative activity was about 50% of the activity at the optimum temperature.

(5) Temperature stability

Figure 3:
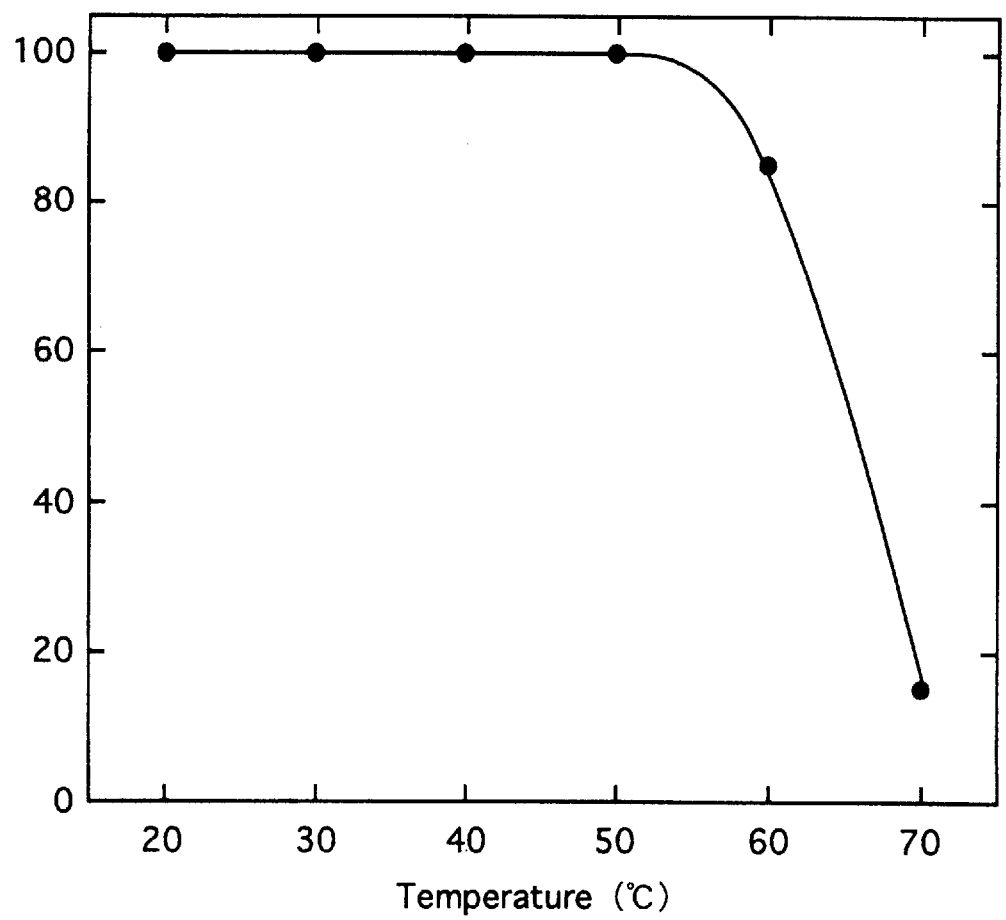
FIG. 3 is a graph illustrating the remaining activity of the lipase produced by the strain SD705 of this invention treated at various temperatures at pH 7 for 1 hour.

Remaining activity after heat retaining treatment at different temperatures in the range of 20° C. to 70° C. at pH 7 for 1 hour was measured by the above-described method for the measurement of activity. The relation between the treating temperature and remaining activity was as shown in FIG. 3. By the treatment at 60° C., 80% or more activity remained. The buffer solution used for the treatment was a mixed buffer solution consisting of 50 mM ε-aminocaproic acid, 50 mM bistris(bis[2-hydroxyethyl]iminotris[hydroxymethyl]methane), and 50 mM TAPS (N-tris[hydroxymethyl]-methyl-3-aminopropanesulfonic acid), with the pH of the buffer solution being adjusted to pH 7 with hydrochloric acid.

(6) pH stability

Figure 4:
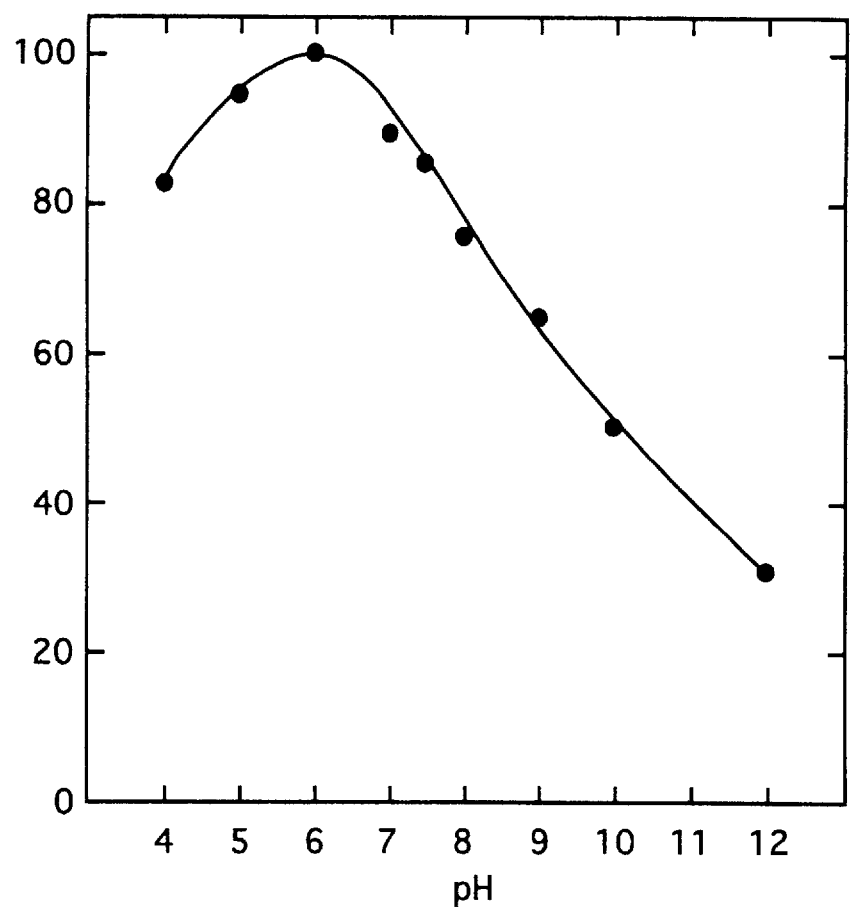
FIG. 4 is a graph illustrating the remaining activity of the lipase produced by the strain SD705 of this invention after 1 hour standing at various pH values at 37° C.

The remaining activity was determined by the above-described titration method after being treated at different pH within the range of pH 4 to 12 at 37° C. for 1 hour. The relation between the treating pH and remaining activity was as shown in FIG. 4. By the treatment at pH 4 to 10, 50% or more activity remained. The buffer solution used for the treatment was mixed buffer solution consisting of 0.5mM calcium chloride, 50 mM ε-aminocaproic acid, 50 mM bistris(bis[2-hydroxyethyl]iminotris[hydroxymethyl]methane), and 50 mM TAPS (N-tris[hydroxymethyl]-methyl-3-aminopropanesulfonic acid), with the pH of the buffer solution being adjusted with hydrochloric acid or sodium hydroxide.

(7) Molecular weight

Molecular weight obtained by SDS-polyacrylamide gel electrophoresis (molecular weight standard: cytochrome C (monomer, dimer, trimer, tetramer, hexamer)) was 31,000±2,000.

(8) Isoelectric point

Isoelectric point measured by isoelectric point polyacrylamide gel electrophoresis was 5.2±0.5.

(9) Influences of the components of detergents

Activities were measured with toriolein emulsion as a substrate in the same manner as the above-described method for the measurement of activity except that there were added various commercially available detergents (4 kinds) in the standard concentration upon use described below and API-21 (Japanese Patent Publication (Kokoku) No. 60-55118 (1985) in a concentration of 0.3 nkat/ml, the reaction pH was 10, and the reaction time was set to 30 minutes. Assuming the activity without addition of a commercially available detergent and API-21 is 100, relative activities were as shown in Table 2. As shown, the lipase of this invention has high activity in various detergent solutions containing protease.

The lipase having the above-described properties functions sufficiently even at low temperatures (60° C. or lower) and exhibits its activity stably in detergent solutions so that it is preferable as a lipase to be blended with detergents.

Detergent Composition

According to this invention, there are provided detergent compositions in which the lipase having the above-described properties is blended. The amount of lipase blended in the detergent compositions of this invention is not limited particularly. Generally, the lipase is blended in proportions of from 100 to 10,000 units, preferably from 500 to 4,000 units, per g of detergent composition. If the blending amount is too small, no sufficient increase in the washing effect can be obtained. On the contrary, if it is too large, an increase in the washing effect relative to the amount of enzyme blended is not high so that it is undesirable from economical viewpoints.

According to this invention, the above-described lipase can be blended with any known detergent composition without changing the composition of the detergent composition. Therefore, no limitation is posed on the detergent composition which can be used in this invention. Representative example of the detergent composition which can be used in this invention includes a detergent composition which consists of 10 to 50% by weight of a surfactant, 0 to 50% by weight of builders, 1 to 50% by weight of alkali agents or inorganic electrolytes, 0.1 to 5% by weight of at least one blending component selected from the group consisting of antiredeposition agents, enzymes, bleaching agents, fluorescent whitening agents, anticaking agents, and antioxidants, the weight percents being based on the weight of the detergent composition.

As the surfactant can be used any surfactant that is usually blended with detergents as one of their components. Examples thereof include soaps, for example, aliphatic sulfates such as straight or branched chain alkyl or alkenyl sulfates, amide sulfates, alkyl or alkenyl ether sulfates having a straight or branched chain alkyl or alkenyl group to which one or more of ethylene oxide, propylene oxide and butylene oxide added, aliphatic sulfonates such as alkyl sulfonates, amide sulfonates, dialkyl sulfosuccinates, sulfonates of α-olefins, of vinylidene-type olefins and of internal olefins, aromatic sulfonates such as straight or branched chain alkylbenzenesulfonates, alkyl or alkenyl ether carbonates or amides having a straight or branched chain alkyl or alkenyl group to which one or more of ethylene oxide, propylene oxide and butylene oxide added, or amides, α-sulfo-fatty acid salts or esters, amino acid type surfactants, phosphate surfactants such as alkyl or alkenyl acidic phosphates, and alkyl or alkenyl phosphates, sulfonic acid type amphoteric surfactants, betaine type amphoteric surfactants, alkyl or alkenyl ethers or alcohols having a straight or branched chain alkyl or alkenyl group to which one or more of ethylene oxide, propylene oxide and butylene oxide added, polyoxyethylenealkyl phenyl ethers having a straight or branched chain alkyl group to which one or more of ethylene oxide, propylene oxide and butylene oxide added, higher fatty acid alkanolamides or alkylene oxide adducts thereof, sucrose fatty acid esters, fatty acid glycerol monoesters, alkyl- or alkenylamine oxides, tetraalkylammonium salt type cationic surfactants and so on. In the case of anionic surfactants, the counter ions are preferably sodium ions or potassium ions. These surfactants are used singly or as mixtures of two or more of them.

The builder and alkali agents or inorganic electrolytes which can be used include phosphates such as orthophosphates, pyrophosphates, tripolyphosphates, metaphosphates, hexametaphosphates, and phytates, phosphonates such as ethane-1,1-diphosphonic acid, ethane-1,1,2-triphosphonic acid, ethane-1-hydroxy-1,1-diphosphonic acid and derivatives thereof, ethanehydroxy-1,1,2-triphosphonic acid, ethane-1,2-dicarboxy-1,2-diphosphonic acid, and methanehydroxyphosphonic acid, phosphonocarboxylates such as salts of 2-phosphonobutane-1,2-dicarboxylic acid, 1-phosphonobutane-2,3,4-tricarboxylic acid, and α-methylphosphonosuccinic acid, amino acid salts such as aspartic acid and glutamic acid, aminopolyacetates such as nitrilotriacetates, ethylenediaminetetraacetates, and diethylenetriaminepentaacetates, high molecular weight electrolytes such as polyacrylic acid, polyitaconic acid, polymaleic acid, maleic anhydride copolymers, and carboxymethylcellulose salts, nondissociated high polymer molecules such as polyethylene glycol, and polyvinyl alcohol, organic acid salts such as salts of diglycolic acid, oxydisuccinic acid, carboxymethyl-oxysuccinic acid, citric acid, lactic acid, tartaric acid, carboxymethylates of sucrose, lactose, etc., carboxymethylate of pentaerythritol, carboxymethylate of gluconate, benzenepolycarboxylic acid, oxalic acid, malic acid, oxydisuccinic acid, gluconic acid and so on, as well as inorganic acid salts such as aluminosilcates such as zeolite, alkali metal salts such as inorganic salts, e.g., carbonates, sesquicarbonates, sulfates, metasilicates, etc. Also, there can be used organic substances such as starch and urea and inorganic compounds such as sodium chloride and bentonite. Furthermore, as the organic alkali agent, there can be used triethanolamine, diethanolamine, monoethanolamine, triisopropanolamine, etc.

As described above, the detergent compositions of this invention contain as essential components surfactants, lipases, alkali agents, or inorganic electrolytes and optional components, for example, amphoteric surfactants, bleaching agents such as sodium percarbonates and sodium perborates, dyes, builders, antiredeposition agents such as polyethylene glycol, polyvinyl alcohol, polyvinyl pyrrolidone, and carboxymethylcellulose, anticaking agents, antioxidants, other enzymes such as protease as needed.

Lipase and other enzymes such as protease may be blended with the detergent compositions of this invention in any method. However, blending them in a state of fine powder is not preferred due to dusting when detergents are handled by users and operators in detergent industries from the viewpoints of safety and hygiene. It is thus preferred that the enzymes be in the form of solutions or molded into shapes which could minimize dusting in advance. The molding can be performed by any of conventionally used methods such as rounding granulation, extrusion granulation, flow granulation, centrifuge granulation or the like. However, the shape of the lipases and other enzymes such as protease to be blended with the detergent compositions of this invention is not limited to those molded by these methods.

BEST MODE FOR CARRYING OUT THE INVENTION

Next, this invention will be described with reference to examples. However, this invention should not be construed as being limited to the following examples. In the following description, all % are by weight unless otherwise indicated.

EXAMPLE 1
Cultivation of lipase-producing bacteria (SD705 strain)

A liquid culture medium (2 ml) containing in concentrations 2% of soybean powder, 0.1% of diammonium hydrogen phosphate, 1% of olive oil, 0.5% of dipotassium hydrogen phosphate, 0.1% of magnesium sulfate heptahydrate, and 0.3% of sodium carbonate was put into a test tube of 18 mm in diameter and sterilized with an autoclave at 121° C. for 20 minutes. Then, a loopful of Pseudomonas sp. SD705 strain was inoculated in the medium and incubated at 35° C. for 24 hours and at 130 rpm. After the incubation, the bacterial cells were removed by centrifugation to obtain a lipase solution. The solution had a lipase activity of 5U/ml.

EXAMPLE 2
Cultivation of lipase-producing bacteria (SD705 strain) and collection of lipase A liquid culture medium (2 liters) containing in concentrations 2% of soybean powder, 0.1% of diammonium hydrogen phosphate, 0.5% of dipotassium hydrogen phosphate, 0.1% of magnesium sulfate heptahydrate, 0.3% of sodium carbonate, and 1.0% of Tween 85 was put into a 5 liter jar fermenter and sterilized with an autoclave at 121° C. for 20 minutes. Then, Pseudomonas sp. SD705 strain was inoculated in the medium and incubated at 35° C. for 24 hours, with stirring at 1000 rpm and under aeration. After the incubation, the bacterial cells were removed by centrifugation to obtain a lipase solution. The solution had a lipase activity of 20U/ml.

The lipase solution was subjected to a ammonium sulfate precipitation method to obtain precipitates of 20 to 40% saturation fraction. The precipitate were desalted and then freeze-dried to obtain powder of lipase.

EXAMPLE 3
Purification of lipase

The powder of lipase obtained in Example 2 was dissolved in a 10% saturated ammonium sulfate solution and chromatographed by hydrophobic chromatography with Butyl-Toyopearl 650M (trade name, Tosoh Ltd.) to obtain active fractions. The active fractions were dialyzed through 10 mM Tris-hydrochloric acid buffer (pH 8) containing 0.3 mM calcium chloride and adsorbed on ion exchange chromatographic resin (DEAE-Cellulofine A-800, trade name, Seikagaku Kogyo Co., Ltd.) equilibrated with the same buffer as above, followed by elution with sodium chloride gradient to obtain active fractions. These were desalted and then freeze-dried to obtain purified enzyme.

The freeze-dried preparation was confirmed to be unique by SDS polyacrylamide gel electrophoresis.

EXAMPLE 4
Comparison of activity in detergent solutions between the lipase of this invention and other lipases The activity in detergent solutions of the raw powder of lipase obtained in Example 2 were measured and the results were compared with the results of measurements of the activities in detergent solutions of the lipase SD2 produced by *Pseudomonas alcaligenes* SD2 strain (ATCC 53877) described in U.S. Pat. No. 5,069,810, and the activities in detergent solutions of the lipases produced by *Pseudomonas pseudoalcaligenes* CBS 467.85 strain, CBS 468.85 strain, CBS 471.85 strain, and CBS 473.85 strain. As the enzyme of *Pseudomonas alcaligenes* SD2 was used a supernatant of the culture broth obtained by cultivating the strain in a culture medium containing 0.5% ammonium sulfate, 0.05% dipotassium hydrogenphosphate, 0.025% of magnesium sulfate heptahydrate, 2.0% tryptone, 1.0 mM polyoxyethylene (20) cetyl ether at 30° C. for 16 hours followed by centrifugation. As the enzymes of the above-described four *Pseudomonas pseudoalcaligenes* strains were used supernatants obtained by cultivating the respective strains in a culture medium containing 10% skimmed milk, pH 7, at 20° C. for 48 hours followed by centrifugation.

The activities of the enzymes were measured in the same manner as the above-described method for the measurement of activities using a triolein emulsion as a substrate except that various commercial detergents (4 kinds) in a standard use concentration and API-21 (Japanese Patent Publication (Kokoku) No. 60–55118), representative alkaline protease for detergents, in a concentration of 0.3 nkat/ml were added, the reaction pH was set to 10, and the reaction time was set to 30 minutes.

The commercially available detergents used included Attack (trade name, produced by Kao Ltd.; an anionic surfactant based detergent containing linear alkylbenzenesulfonate sodium salt, sodium alkylsulfate, and polyoxyethylene alkyl ether), Ultra Ariel (trade name, produced by Procter and Gamble Far East Co.; an anionic surfactant based detergent containing linear alkylbenzenesulfonic acid sodium salt, sodium alkylsulfate, sodium alkanoyloxybenzenesulfonate and polyoxyethylene alkyl ether), Ultra Tide (trade name, produced by Procter and Gamble Co.; an anionic surfactant based detergent), and Fresh Start (trade name, Colgate-Palmolive Co.; a nonionic surfactant based detergent). The detergents were added in a standard use concentration so that there were, in final concentrations, 833 ppm of Attack, 1,000 ppm of Ultra-Ariel, 1,000 ppm of Ultra Tide, and 624 ppm of Fresh Start.

Assuming the activity of the detergent without adding commercially available detergents and API-21 is 100, relative activities are shown in Table 2.

TABLE 2

| | Activity in detergent solutions (%) | | | | |
|---|---|---|---|---|---|
| Enzyme | | | Detergent | | |
| producing strain | No detergent | Attack | Ultra Ariel | Ultra Tide | Fresh Start |
| SD705 | 100 | 78 | 84 | 57 | 98 |
| ATCC 53877 | 100 | 31 | 29 | 33 | 80 |
| CBS 467.85 | 100 | 17 | 18 | 29 | 102 |
| CBS 468.85 | 100 | 54 | 50 | 55 | 62 |
| CBS 471.85 | 100 | 20 | 16 | 35 | 85 |
| CBS 473.85 | 100 | 50 | 49 | 40 | 95 |

Table 2 shows that the lipase of this invention exhibits higher activity than the other lipases in the detergent solutions.

Among the other lipases, there are some which show relative activities equivalent to that of the lipase of this invention. However, their relative activities decrease significantly for different kinds of detergents (enzymes derived from CBS 467.85 and CBS 468.85). On the contrary, the lipase of this invention has the feature that it shows high relative activity regardless of the kind of detergent.

EXAMPLE 5
Detergent Composition and Evaluation of Washing

A detergent composition containing the lipase of this invention was prepared by blending 2400 units/g of the powder of lipase obtained in Example 2 with Attack, a commercially available detergent.

Evaluation of washing was performed as follows. That is, soiled test cloths were used which were degreased cotton cloth (15 cm×15 cm) spotted with 70 mg of triolein dissolved in benzene and dried overnight at room temperature. The washing apparatus used was Terg-O-Tometer. In 1 liter of distilled water containing calcium chloride in a final concentration of 50 ppm were dissolved the above-described lipase-blended detergent composition and Attack, commercially available detergent, each in a standard use concentration. In the case of the former, the concentration of lipase in the solution was 2 units/ml. Further, protease API-21 (Japanese Patent Publication (Kokoku) No. 60-55448 (1985)) was added in a concentration of 0.3 nkat/ml. Six pieces of the triolein-contaminated cloth per liter of the washing solution were placed in the detergent solution and washing was performed at a washing temperature of 30° C. at 120 rpm for 30 minutes. After the washing, the cloth pieces were rinsed twice, each for 3 minutes with 1 liter of the above-described calcium-added distilled water, followed by drying at room temperature. The amount of triolein on unwashed and washed cloth pieces was determined by the above described TLC-FID method after extraction of triolein with n-hexane. Washing efficiencies were obtained according to the following formula. Washing efficiency (%)={ (Amount of triolein on unwashed soiled test cloth−amount of triolein on washed soiled test cloth)/amount of triolein on unwashed soiled test cloth}×100

Table 3 shows the results obtained.

TABLE 3

| | Evaluation of Washing | |
|---|---|---|
| | Addition of lipase of this invention | No addition of lipase |
| Washing efficiency (%) | 78.4 | 68.5 |

As shown in Table 3, washing with the detergent containing the lipase of this invention gave rise to higher washing efficiency than washing with the detergent containing no such lipase.

EXAMPLE 6
Detergent Composition and Evaluation of Washing

Three kinds of detergent compositions were prepared. That is, a lipase-blended detergent composition consisting of All (Lever Brothers Co., trade name) and 2,400 units/g of the powder of lipase obtained in Example 2, protease-blended detergent composition consisting of All and 270 nkat/g of the powder of Protease API-21 (Japanese Patent Publication (Kokoku) No. 60-55448 (1985)), and lipase/ protease-blended detergent composition consisting of All and 2,400 units/g of the powder of lipase obtained in Example 2 and powder of Protease API-21 in an amount of 270 nkat/g were prepared.

Evaluation of washing was performed as follows. That is, soiled test cloths were used which were commercially available soiled test cloth EMPA 112. The washing apparatus used was Terg-O-Tometer. In 1 liter of distilled water containing calcium chloride in a final concentration of 50 ppm were dissolved each of the above-described detergent compositions and All, commercially available detergent, each in a standard use concentration (final concentration of 1100 ppm). In the case of the lipase-blended detergent composition, the concentration of lipase in the solution was 2.6 units/ml. In the case of protease-blended detergent composition, the concentration of protease in the solution was 0.3 nkat/ml. Six pieces of the described soiled test cloth per liter of the washing solution were placed in the detergent solution and washing was performed at a washing temperature of 30° C. at 120 rpm for 30 minutes. After the washing, the cloth pieces were rinsed twice, each for 3 minutes with 1 liter of the above-described calcium-added distilled water, followed by drying at room temperature. The reflectivity (460 nm) of the soiled test cloth pieces was measured. Effect of addition of enzymes to washing was expressed in terms of difference between the reflectivity obtained by washing with the enzyme-blended detergent compositions and that of the detergent without addition of such an enzyme. Table 4 shows the results obtained.

TABLE 4

Evaluation of Washing

| Detergent Composition | Effect of addition of enzyme |
| --- | --- |
| Lipase-blended | 8.2 |
| Protease-blended | 9.8 |
| Lipase/protease-blended | 15.6 |

In washing with the detergent containing the lipase of this invention gave rise to higher washing effect than washing with the detergent containing no such lipase regardless of whether protease is added or not.

ADVANTAGEOUS EFFECTS OF THIS INVENTION

The lipase of this invention retains high stability and high activity in solutions of various commercially available detergents and in copresence of detergent components such as surfactants, protease and so on and, hence, it can decompose and remove fat and oil efficiently under washing conditions so that it can enhance the washing power of detergents when blended therewith.

*Pseudomonas sp.* SD705 strain and bacteriological equivalents thereof, and variants of these strains according to this invention are useful for producing the lipase of this invention efficiently.

Furthermore, the method of producing the lipase having the above-described properties by the use of such bacterial strains according to this invention is advantageous in that the lipase can be produced efficiently.

Blending the lipase of this invention with detergents provides detergent compositions having excellent washing characteristics.

Also, blending the lipase of this invention together with other enzymes with detergents provides detergent compositions having excellent washing characteristics.

What is claimed is:

1. A lipase obtained from Pseudomonas strain SD 705, wherein said lipase has the following properties:

(a) an pH optimum in the range of 10–11, measured at a temperature in the range of 30° C. to 80° C. using the triolein emulsion as a substrate; and (b) a temperature optimum in the range of from 55° C. to 65° C.

2. The lipase of claim 1, wherein said enzyme is further characterized as having an operating pH in the range of from 3.5 to 12.

3. The lipase of claim 1, wherein said enzyme is further characterized as having a molecular weight of about 31,000±2,000, measured by SDS-polyacrylamide gel electrophoresis.

4. The lipase of claim 1, wherein said enzyme is further characterized as having an isolectric point of about 5.2±0.5, measured by isoelectric point polyacrylamide gel electrophoresis.

5. The lipase of claim 1, wherein the Pseudomonas strain is FERM BP-4772.

6. A method of producing a lipase comprising the steps of:

(a) cultivating a bacteria belonging to the genus Pseudomonas; and (b) recovering the lipase of claim 9 from a culture broth of the bacteria.

7. A detergent composition comprising the lipase of claim 1.

* * * * *